United States Patent
Okazaki et al.

(10) Patent No.: US 7,176,323 B2
(45) Date of Patent: Feb. 13, 2007

(54) PROCESS FOR THE PRODUCTION OF γ-KETO ACETALS

(75) Inventors: Rei Okazaki, Hiratsuka (JP); Shunshi Kojima, Kamakura (JP)

(73) Assignee: Sankyo Company, Limited, Tokyo (JP)

( * ) Notice: Subject to any disclaimer, the term of this patent is extended or adjusted under 35 U.S.C. 154(b) by 174 days.

(21) Appl. No.: 11/055,645

(22) Filed: Feb. 9, 2005

(65) Prior Publication Data
US 2005/0148780 A1 Jul. 7, 2005

Related U.S. Application Data

(63) Continuation of application No. PCT/JP03/10471, filed on Aug. 19, 2003.

(30) Foreign Application Priority Data

Aug. 20, 2002 (JP) ............... 2002-238786
May 9, 2003 (JP) ............... 2003-131270

(51) Int. Cl.
C07D 207/323 (2006.01)
C07D 319/06 (2006.01)
(52) U.S. Cl. ..................... 548/563; 549/375
(58) Field of Classification Search ............ 548/563; 549/375
See application file for complete search history.

(56) References Cited

U.S. PATENT DOCUMENTS

| | | | |
|---|---|---|---|
| 5,908,858 A | 6/1999 | Kimura et al. | |
| 5,935,990 A | 8/1999 | Khanna et al. | |

FOREIGN PATENT DOCUMENTS

| | | |
|---|---|---|
| EP | 0 799 823 A1 | 10/1997 |
| JP | 2000-80078 A | 3/2000 |

OTHER PUBLICATIONS

March J., *Advanced Organic Chemistry*, (1985), 3rd Ed., pp. 789-791.

Khanna I.K.; Weier R.M.; Yu Y.; Collins P.W.; Miyashiro J.M.; Koboldet C.M.; Veenhuizen A.Q.; Currie, J.L.; Seibert K.; Isakson P.C., "1,2-Diarylpyrroles as Potent and Selective Inhibitors of Cyclooxygenase-2", *J. Med. Chem.*, (1997), vol. 40, pp. 1619 to 1633.

English-language International Preliminary Examination Report dated Feb. 18, 2004 of International application PCT/JP2003/010471 filed Aug. 19, 2003; Applicant: Sankyo Company, Limited.

*Primary Examiner*—Taofiq Solola
(74) *Attorney, Agent, or Firm*—Frishauf, Holtz, Goodman & Chick, P.C.

(57) ABSTRACT

A process for the production of a γ-ketoacetal compound wherein the desired product is obtained by a simple procedure in a high yield as a high purity product. The reaction scheme for the process is as follows:

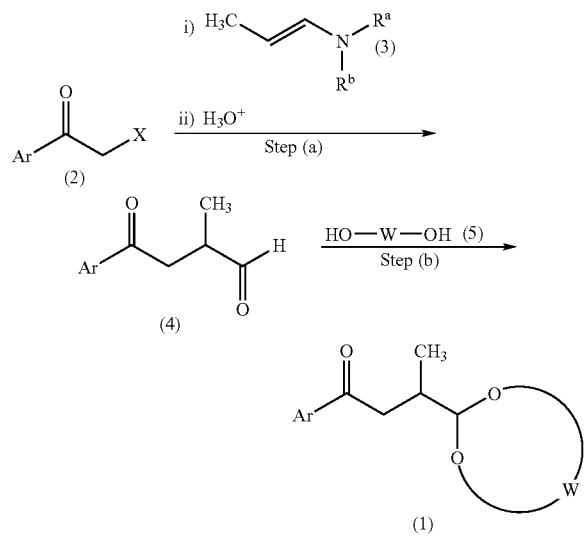

wherein Ar is an aryl group; X is a halogen atom; $R^a$ and $R^b$ is an alkyl or alkoxy group; and W is an alkylene group.

15 Claims, No Drawings

PROCESS FOR THE PRODUCTION OF γ-KETO ACETALS

CROSS-REFERENCE TO RELATED APPLICATION

This application is a continuation application of International application PCT/JP2003/010471 filed on Aug. 19, 2003, the entire contents of which are hereby incorporated by reference herein.

FIELD OF THE INVENTION

The present invention relates to a process for producing γ-ketoacetal compounds.

BACKGROUND OF THE INVENTION

The γ-ketoacetal compounds of general formula (A) shown below are known as intermediates for producing a 4-methyl-1,2-diarylpyrrole derivative (Japanese Patent Publication (Kokai) Number 2000-80078) which is known as a useful analgesic (see U.S. Pat. No. 5,908,858)

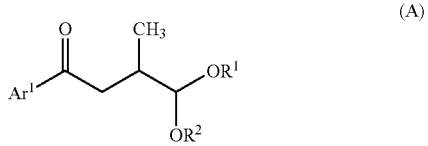
(A)

(wherein $Ar^1$ represents an aryl group which may be optionally substituted with a substituent(s), $R^1$ and $R^2$ each independently represent a lower alkyl group or $R^1$ and $R^2$ taken together represent a trimethylene group or the like). The process for producing said γ-ketoacetal compounds, wherein nitromethane ($CH_3NO_2$) and a base are used, is documented (Japanese Patent Publication (Kokai) Number 2000-80078). Since nitromethane is apt to explode, the process must be carefully carried out. There are hence some considerable problems in the process; for example, the process for preparation of γ-ketoacetal compounds, especially in a large-scale production, becomes particularly complex in order to avoid explosions occurring.

SUMMARY OF THE INVENTION

The inventors have investigated a process for the production of γ-ketoacetal compounds, found a process for production of them by using an enamine derivative, but not nitromethane, and obtained the desired product with high purity by a simple procedure with good yields, and thus completed the present invention.

The present invention relates to (1) a process for the production of a compound of general formula (1) by reacting a compound of general formula (2)

(2)

(wherein Ar represents a $C_6$–$C_{10}$ aryl group or a $C_6$–$C_{10}$ aryl group substituted with a substituent(s) independently selected from Substituent group α; Substituent group α consists of halogen atoms, $C_1$–$C_6$ alkyl groups, halogenated $C_1$–$C_6$ alkyl groups, hydroxyl groups, $C_1$–$C_6$ alkoxy groups, $C_1$–$C_6$ alkylthio groups, mercapto groups, $C_1$–$C_6$ alkylsulfonyl groups, and sulfamoyl groups; and X represents a halogen atom) with a compound of general formula (3)

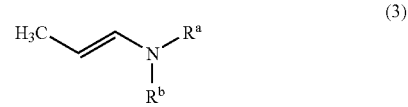
(3)

(wherein $R^a$ and $R^b$ are the same or different and each represents independently a $C_1$–$C_6$ alkyl group, a $C_1$–$C_6$ alkyl group substituted with a $C_1$–$C_6$ alkoxy group(s), or a $C_3$–$C_6$ cycloalkyl group, or $R^a$ and $R^b$ taken together represent a $C_4$–$C_8$ alkylene group) in an inert solvent and hydrolyzing the product with an acid to afford a compound of general formula (4),

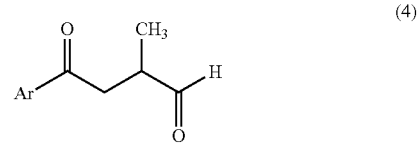
(4)

(wherein Ar has the same meaning as that indicated above), followed by reacting the compound of general formula (4) with a compound of general formula (5)

(5)

(wherein W represents a $C_1$–$C_6$ alkylene group) in the presence of an acid to give a compound of general formula (1)

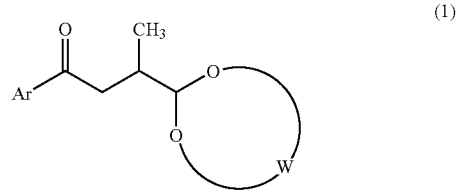
(1)

(wherein Ar and W have the same meanings as those indicated above).

Among the above processes, the preferred processes are:

(2) a process wherein Ar is a phenyl group or a phenyl group substituted with a substituent(s) independently selected from Substituent group α, (3) a process wherein Ar is a phenyl group or a phenyl group substituted with a substituent(s) independently selected from the substituent group consisting of methyl, methoxy, ethoxy and methylthio groups, (4) a process wherein Ar is a 4-methylphenyl, 3-methylphenyl, 4-methoxyphenyl, 4-ethoxyphenyl, 4-methylthiophenyl, 3,4-dimethylphenyl, or 3,4-dimethoxyphenyl group, (5) a process wherein X is a bromine atom or an iodine atom, (6) a process wherein X is a bromine atom,
(7) a process wherein $R^a$ and $R^b$ are the same or different and each represents independently a $C_2$–$C_5$ alkyl group, a $C_2$–$C_5$ alkyl group substituted with a $C_1$–$C_4$ alkoxy group (s), or a $C_4$–$C_6$ cycloalkyl group,
(8) a process wherein $R^a$ and $R^b$ are the same or different and each represents independently an isopropyl, isobutyl, isopentyl, 2-methoxyethyl, 3-methoxypropyl, 2-ethoxyethyl, cyclopentyl, or cyclohexyl group,
(9) a process wherein $R^a$ and $R^b$ are both an isobutyl group,
(10) a process wherein W is a straight or branched chain $C_3$–$C_5$ alkylene group,
(11) a process wherein W is a straight chain $C_3$–$C_5$ alkylene group, and
(12) a process wherein W is a 2-methyltrimethylene or 2,2-dimethyltrimethylene group.

Furthermore, the present invention provides
(13) a process for the production of a compound of general formula (7)

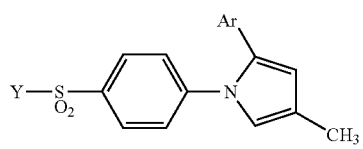

(wherein Ar represents a $C_6$–$C_{10}$ aryl group or a $C_6$–$C_{10}$ aryl group substituted with a substituent(s) independently selected from Substituent group α; Substituent group α consists of halogen atoms, $C_1$–$C_6$ alkyl groups, halogenated $C_1$–$C_6$ alkyl groups, hydroxyl groups, $C_1$–$C_6$ alkoxy groups, $C_1$–$C_6$ alkylthio groups, mercapto groups, $C_1$–$C_6$ alkylsulfonyl groups, and sulfamoyl groups; and Y represents a methyl or amino group (preferably an amino group)) that includes a process for the production of a compound of general formula (4) by reacting a compound of general formula (2)

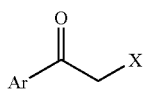

(wherein Ar represents a $C_6$–$C_{10}$ aryl group or a $C_6$–$C_{10}$ aryl group substituted with a substituent(s) independently selected from Substituent group α; Substituent group α consists of halogen atoms, $C_1$–$C_6$ alkyl groups, halogenated $C_1$–$C_6$ alkyl groups, hydroxyl groups, $C_1$–$C_6$ alkoxy groups, $C_1$–$C_6$ alkylthio groups, mercapto groups, $C_1$–$C_6$ alkylsulfonyl groups, and sulfamoyl groups; and X represents a halogen atom) with a compound of general formula (3)

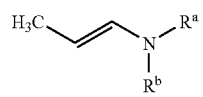

(wherein $R^a$ and $R^b$ are the same or different and each represents independently a $C_1$–$C_6$ alkyl group, a $C_1$–$C_6$ alkyl group substituted with a $C_1$–$C_6$ alkoxy group(s), or a $C_3$–$C_6$ cycloalkyl group, or $R^a$ and $R^b$ taken together represent a $C_4$–$C_8$ alkylene group) in an inert solvent and hydrolyzing the product with an acid to afford a compound of general formula (4)

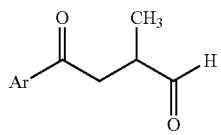

(wherein Ar has the same meaning as that indicated above), and that further includes a process for the production of a compound of general formula (1) by reacting a compound of general formula (4) with a compound of general formula (5)

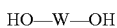

(wherein W represents a $C_1$–$C_6$ alkylene group) in the presence of an acid to afford a compound of general formula (1)

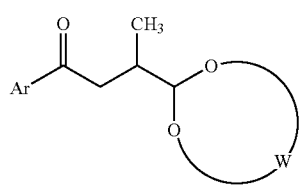

(wherein Ar and W have the same meanings as those indicated above), and (14) a process for the production of a compound of general formula (7)

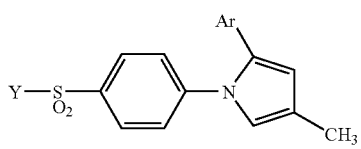

(wherein Ar represents a $C_6$–$C_{10}$ aryl group or a $C_6$–$C_{10}$ aryl group substituted with a substituent(s) independently selected from Substituent group α; Substituent group α consists of halogen atoms, $C_1$–$C_6$ alkyl groups, halogenated $C_1$–$C_6$ alkyl groups, hydroxyl groups, $C_1$–$C_6$ alkoxy groups, $C_1$–$C_6$ alkylthio groups, mercapto groups, $C_1$–$C_6$ alkylsulfonyl groups, and sulfamoyl groups; and Y represents a methyl or amino group (preferably an amino group)) by reacting a compound of general formula (2)

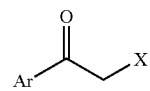

(wherein Ar represents a $C_6$–$C_{10}$ aryl group or a $C_6$–$C_{10}$ aryl group substituted with a substituent(s) independently selected from Substituent group α; Substituent group α consists of halogen atoms, $C_1$–$C_6$ alkyl groups, halogenated $C_1$–$C_6$ alkyl groups, hydroxyl groups, $C_1$–$C_6$ alkoxy groups, $C_1$–$C_6$ alkylthio groups, mercapto groups, $C_1$–$C_6$ alkylsulfonyl groups, and sulfamoyl groups; and X represents a halogen atom) with a compound of general formula (3)

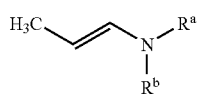
(3)

(wherein $R^a$ and $R^b$ are the same or different and each represents independently a $C_1$–$C_6$ alkyl group, a $C_1$–$C_6$ alkyl group substituted with a $C_1$–$C_6$ alkoxy group(s), or a $C_3$–$C_6$ cycloalkyl group; or $R^a$ and $R^b$ taken together represent a $C_4$–$C_8$ alkylene group) in an inert solvent; hydrolyzing the product with an acid to afford a compound of general formula (4)

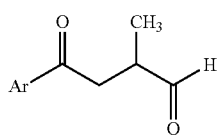
(4)

(wherein Ar has the same meaning as that indicated above); and reacting the compound of general formula (4) with a compound of general formula (5)

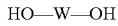
HO—W—OH (5)

(wherein W represents a $C_1$–$C_6$ alkylene group) in the presence of an acid to afford a compound of general formula (1)

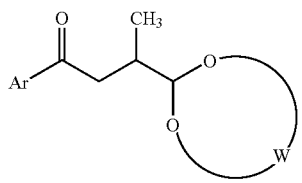
(1)

(wherein Ar and W have the same meanings as those indicated above); followed by reacting the compound of general formula (1) with a compound of general formula (6)

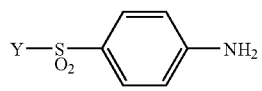
(6)

(wherein Y represents a methyl or amino group (preferably an amino group)) to give a compound of general formula (7).

DETAILED DESCRIPTION OF THE INVENTION

The terms of "$C_6$–$C_{10}$ aryl group", "halogen atom", "$C_1$–$C_6$ alkyl group", "halogenated $C_1$–$C_6$ alkyl group", "$C_1$–$C_6$ alkoxy group", "$C_1$–$C_6$ alkylthio group", "$C_1$–$C_6$ alkylsulfonyl group", "$C_3$–$C_6$ cycloalkyl group", "$C_4$–$C_8$ alkylene group" and "$C_1$–$C_6$ alkylene group", which are used in this specification to specify the present invention, are defined below.

The "$C_6$–$C_{10}$ aryl group" moiety of "$C_6$–$C_{10}$ aryl group" and "$C_6$–$C_{10}$ aryl group substituted with a substituent(s) independently selected from Substituent group α" in the definition of Ar is a phenyl or naphthyl group and preferably a phenyl group. In addition, the "$C_6$–$C_{10}$ aryl group" described above may be optionally fused to a $C_3$–$C_{10}$ cycloalkyl group (preferably $C_{5-6}$ cycloalkyl group), for example, a fused aryl group is a 5-indanyl group.

The "$C_6$–$C_{10}$ aryl group substituted with a substituent(s) independently selected from Substituent group α" in the definition of Ar is preferably a $C_6$–$C_{10}$ aryl group substituted with one to four substituents independently selected from Substituent group α, more preferably a $C_6$–$C_{10}$ aryl group substituted with one to three substituents independently selected from Substituent group α, and still more preferably a $C_6$–$C_{10}$ aryl group substituted with one or two substituents independently selected from Substituent group α.

The "halogen atom" in the definitions of Substituent group α and X is a fluorine atom, a chlorine atom, a bromine atom, or an iodine atom. The preferred halogen atom in Substituent group α is a fluorine atom, a chlorine atom, or a bromine atom and still more preferably a fluorine atom or a chorine atom. The preferred halogen atom in X is a bromine atom or an iodine atom, particularly more preferably a bromine atom. The "$C_1$–$C_6$ alkyl group" in the definitions of Substituent group α, $R^a$ and $R^b$, and the alkyl moiety of the "$C_1$–$C_6$ alkyl group substituted with a $C_1$–$C_6$ alkoxy group(s)" in the definitions of $R^a$ and $R^b$ are each independently a straight or branched chain alkyl group such as a methyl, ethyl, propyl, isopropyl, butyl, isobutyl, s-butyl, tert-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, or 2-ethylbutyl group. The alkyl group in Substituent group α is preferably a straight or branched chain $C_1$–$C_4$ alkyl group, more preferably a methyl, ethyl, propyl, isopropyl, or butyl group, still more preferably a methyl, ethyl, or propyl group, and most preferably a methyl group. The alkyl groups in $R^a$ and $R^b$ are preferably each independently a straight or branched chain $C_2$–$C_5$ alkyl group, more preferably an ethyl, propyl, isopropyl, butyl, isobutyl, or isopentyl group, still more preferably an isopropyl, isobutyl, or isopentyl group, and most preferably an isobutyl group.

The "halogenated $C_1$–$C_6$ alkyl group" in the definition of Substituent group α is a "$C_1$–$C_6$ alkyl group" as indicated above in which one or more hydrogen atoms are substituted with a halogen atom(s) indicated above, and preferably a halogenated $C_1$–$C_4$ alkyl group, more preferably a trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl, or 2,2-dibromoethyl group, more preferably a trifluoromethyl, trichloromethyl, difluoromethyl, or fluoromethyl group, and most preferably a trifluoromethyl group.

The "$C_1$–$C_6$ alkoxy group" in the definition of Substituent group α and the "alkoxy group moiety" of the "$C_1$–$C_6$ alkyl group substituted with a $C_1$–$C_6$ alkoxy group(s)" in the definition of $R^a$ and $R^b$ are each independently a "$C_1$–$C_6$ alkyl group" as indicated above to which an oxygen atom is attached, preferably a straight or branched chain $C_1$–$C_4$ alkoxy group, more preferably a methoxy, ethoxy, propoxy, isopropoxy, or butoxy group, still more preferably a methoxy, ethoxy, or propoxy group, and most preferably an ethoxy group.

The "$C_1$–$C_6$ alkylthio group" in the definition of Substituent group α is a "$C_1$–$C_6$ alkyl group" as indicated above to which a sulfur atom is attached, preferably a straight or branched chain $C_1$–$C_4$ alkylthio group, more preferably a methylthio, ethylthio, propoylthio, isopropoylthio, or butylthio group, and still more preferably a methylthio, ethylthio, or propylthio group.

The "$C_1$–$C_6$ alkylsulfonyl group" in the definition of Substituent group α is a "$C_1$–$C_6$ alkyl group" as indicated above to which a sulfonyl group (—$SO_2$—) is attached, preferably a straight or branched chain $C_1$–$C_4$ alkylsulfonyl group, more preferably a methylsufonyl, ethylsulfonyl, propylsulfonyl, isopropylsulfonyl, or butylsulfonyl group, still more preferably a methylsulfonyl, ethylsulfonyl, or propylsulfonyl group, and most preferably a methylsulfonyl group.

The "$C_3$–$C_6$ cycloalkyl groups" in the definitions of the $R^a$ and $R^b$ are each independently a cyclopropyl, cyclobutyl, cyclopentyl, or cyclohexyl group, preferably a $C_4$–$C_6$ cycloalkyl group, and more preferably a cyclopentyl or cyclohexyl group.

The "$C_4$–$C_8$ alkylene group" that is formed by $R^a$ and $R^b$ taken together is a tetramethylene, 1-methyltrimethylene, 2-methyltrimethylene, 1,1-dimethylethylene, pentamethylene, 1,1-dimethyltrimethylene, 2,2-dimethyltrimethylene, 1,2-dimethyltrimethylene, hexamethylene, 2-methylpentamethylene, heptamethylene, or 2,4-dimethylpentamethylene group, preferably a straight or branched chain $C_4$–$C_6$ alkylene group, more preferably a tetramethylene or pentamethylene group, and still more preferably a tetramethylene group.

The "$C_1$–$C_6$ alkylene group" in the definition of W is a straight or branched chain alkylene group such as a methylene, ethylene, trimethylene, propylene, tetramethylene, 1-methyltrimethylene, 2-methyltrimethylene, 1,1-dimethylethylene, pentamethylene, 1,1-dimethyltrimethylene, 2,2-dimethyltrimethylene, 1,2-dimethyltrimethylene, or hexamethylene group, and preferably a straight or branched chain $C_3$–$C_5$ alkylene group, more preferably a trimethylene, 2-methyltrimethylene, or 2,2-dimethyltrimethylene group, still more preferably a trimethylene or 2,2-dimethyltrimethylene group, and most preferably a 2,2-dimethyltrimethylene group.

The definitions of Ar, X, W, and Substituent group α are as indicated above and preferred Ar, X, W, and Substituent group α among these definitions are shown below. Ar is preferably a phenyl group or a phenyl group substituted with a substituent(s) independently selected from Substituent group α; more preferably a phenyl or a phenyl group substituted with a substituent(s) independently selected from the substituent group consisting of methyl, methoxy, ethoxy and methylthio groups; still more preferably a phenyl group substituted with a substituent(s) independently selected from the substituent group consisting of methyl, methoxy, ethoxy and methylthio groups; particularly more preferably a 4-methylphenyl, 3-methylphenyl, 4-methoxyphenyl, 4-ethoxyphenyl, 4-methylthiophenyl, 3,4-dimethylphenyl, or 3,4-dimethoxyphenyl group; and most preferably a 4-ethoxyphenyl or 3,4-dimethylphenyl group.

X is preferably a bromine atom or an iodine atom and most preferably a bromine atom.

W is preferably a straight or branched chain $C_3$–$C_5$ alkylene group, more preferably a straight chain $C_3$–$C_5$ alkylene group, still more preferably a trimethylene, 2-methyltrimethylene, or 2,2-dimethyltrimethylene group, particularly more preferably a trimethylene or 2,2-dimethyltrimethylene group, and most preferably a 2,2-dimethyltrimethylene group.

Substituent group α preferably consists of $C_1$–$C_4$ alkyl groups, $C_1$–$C_4$ alkoxy groups, and $C_1$–$C_4$ alkylthio groups, more preferably consists of methyl, methoxy, ethoxy and methylthio groups, and most preferably consists of a methyl or ethoxy group.

The process for the production of a γ-ketoacetal compound is carried out as shown below.

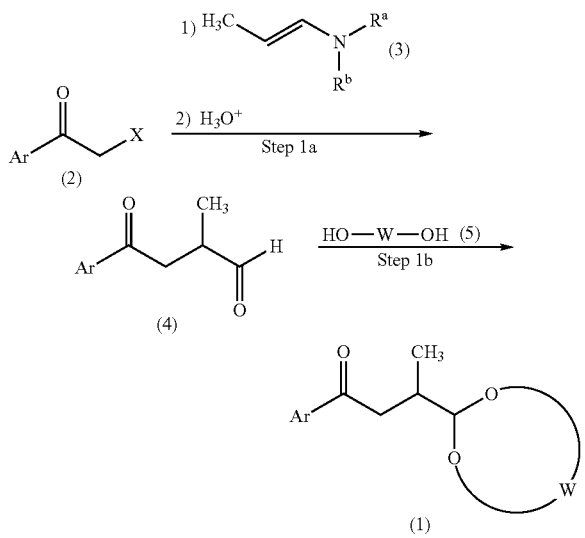

(wherein Ar, $R^a$, $R^b$, X, and W have the same meanings as those indicated above). The step 1a is a process for the production of a dioxo compound of formula (4) which process comprises reacting a phenacyl halide compound of formula (2) with an enamine compound of formula (3) in an inert solvent in the presence or absence of a base, followed by hydrolyzing the reaction mixture using an acid to give the dioxo compound of formula (4).

The inert solvent used in the step 1a is, for example, an aliphatic hydrocarbon such as pentane, hexane, or heptane; an aromatic hydrocarbon such as benzene, toluene, or xylene; a halogenated hydrocarbon such as dichloromethane, chloroform, carbon tetrachloride, or dichloroethane; an ether such as diethyl ether, diisopropyl ether, tetrahydrofuran, or dioxane; an alcohol such as methanol, ethanol, propanol, isopropanol, butanol, s-butanol, isobutanol, or t-butanol; an aprotic polar solvent such as N,N-dimethylformamide, N,N-dimethylacetamide, or dimethyl sulfoxide; a nitrile such as acetonitrile, or an ester such as methyl acetate, or ethyl acetate. The preferred solvent is an aprotic polar solvent or a nitrile and the more preferred one is N,N-dimethylacetamide or acetonitrile.

The base used in step 1a is an organic amine such as pyridine, picoline, 4-(N,N-dimethylamino)pyridine, triethylamine, tributylamine, diisopropylethylamine, or N-methylpiperidine, and it is preferably triethylamine, tributylamine, or diisopropylethylamine.

The reaction temperature is between −30° C. and 200° C. (preferably between 0° C. and 100° C.). The reaction time depends on the reaction temperature and the like and is usually from 30 minutes to 30 hours (preferably from 1 hour to 20 hours).

After the reaction of a phenacyl halide compound of the formula (2) with an enamine compound of the formula (3), a dioxo compound of the formula (4) is produced by the addition of an acid to the reaction mixture. The acid used in the step 1a is an inorganic acid such as hydrogen chloride, hydrobromic acid, sulfuric acid, perchloric acid, or phosphoric acid; or an organic acid such as acetic acid, formic acid, oxalic acid, methanesulfonic acid, para-toluenesulfonic acid, trifluoroacetic acid, or trifluoromethanesulfonic acid, and it is preferably sulfuric acid, hydrogen chloride, or para-toluenesulfonic acid.

After the reaction the desired product in the step 1a is isolated from the reaction mixture according to a conventional procedure.

For example, the desired product is precipitated by cooling the reaction mixture, or the reaction mixture is appropriately neutralized, and when there are insoluble materials in the reaction mixture, the materials are removed by filtration of the reaction mixture; water is added to the reaction mixture; the mixture is extracted with an organic solvent immiscible with water such as toluene; the extract is washed with water, dried over anhydrous magnesium sulfate or the like and the solvent is removed by distillation to give the desired product. The product thus obtained, if necessary, can be further purified by a conventional procedure, for example, silica gel column chromatography.

The dioxo compound of the formula (4) obtained in the step 1a may be used in the next step (step 1b) without purification.

The step 1b is a process for the production of a compound of formula (1) which process comprises reacting a dioxo compound of formula (4) with a glycol compound of formula (3) in an inert solvent (which has the same meaning as that indicated in the step 1a) in the presence of an acid (which has the same meaning as that indicated in the step 1a) to give the compound of formula (1).

The reaction temperature is usually between −70° C. and 100° C., preferably between −30° C. and 60° C. The reaction time is usually from 10 minutes to 20 hours, preferably from 30 minutes to 2 hours.

After the reaction the desired product in the step 1b is isolated from the reaction mixture according to a conventional procedure. For example, the desired product is precipitated by cooling the reaction mixture, or the reaction mixture is appropriately neutralized, and when there are insoluble materials in the reaction mixture the materials are removed by filtration of the reaction mixture; water is added to the reaction mixture; the mixture is extracted with an organic solvent immiscible with water such as toluene; the extract is washed with water, dried over anhydrous magnesium sulfate or the like and the solvent is removed by distillation to give the desired product.

The product thus obtained, if necessary, can be further purified by a conventional procedure, for example, silica gel column chromatography.

The starting materials of the present invention of the compounds of formulae (2), (3) and (5) are known and the compounds of formulae (2) and (3) are, for example, disclosed in the U.S. Pat. No. 5,908,858.

A 4-methyl-1,2-diarylpyrrole derivative of the formula (7) can be prepared by carrying out the following reaction using a compound of formula (1) obtained by the procedure indicated above,

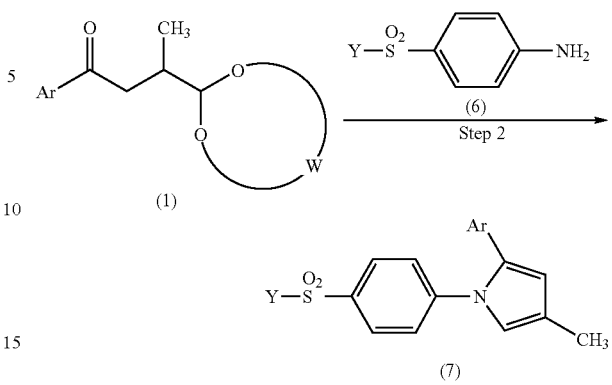

(wherein Ar and W have the same meanings as those indicated above, and Y represents a methyl or amino group).

The step 2 is a process for the production of a 1,2-diarylpyrrole compound of formula (7) which process comprises ring-closing of a compound of formula (1) with an aniline compound of formula (6) by means of a coupling reaction with dehydration in an inert solvent in the presence or absence of an acid to give a compound of formula (7).

The solvent used in the step 2 is not particularly restricted provided that it has no adverse effect on the reaction and can dissolve the starting material to some extent, for example, it is an aliphatic hydrocarbon such as hexane, heptane or petroleum ether; an aromatic hydrocarbon such as benzene, toluene, or xylene; a halogenated hydrocarbon such as methylene chloride, chloroform, carbon tetrachloride, or dichloroethane; an ether such as diethyl ether, diisopropyl ether, tetrahydrofuran, or dioxane; an alcohol such as methanol, ethanol, propanol, isopropanol, or butanol; a nitrile such as acetonitrile, an organic acid such as formic acid, acetic acid, or propionic acid; or water or a mixture of these plural solvents. The preferred solvent is a mixture of an alcohol and water and the more preferred one is a mixture of propanol and water.

The acid used in step 2 is an inorganic acid such as hydrochloric acid or sulfuric acid; or an organic acid such as acetic acid, trifluoroacetic acid, methanesulfonic acid, para-toluenesulfonic acid, or trifluoromethanesulfonic acid, preferably an organic acid, more preferably acetic acid or para-toluenesulfonic acid, and most preferably para-toluenesulfonic acid. The amount of the acid used in step 2 is between 0.01 and 50 equivalents, preferably between 0.05 and 20 equivalents, and more preferably between 0.1 and 10 equivalents.

The amount of the aniline compound of formula (6) is between 1 and 10 equivalents for one equivalent of the compound of formula (1) and preferably between 1 and 3 equivalents.

The reaction temperature depends on the solvent used in the step 2. It is usually between 0° C. and 200° C. and preferably between room temperature and 150° C. The reaction time depends on the reaction temperature or the like and is usually from 10 minutes to 48 hours and preferably from 30 minutes to 15 hours.

In addition, the reaction of step 2 may be carried out with removal of water formed during the reaction; however, usually it can be conducted without removal of the water.

After the reaction of the step 2, the desired product is isolated from the reaction mixture according to a conventional procedure. For example, the reaction mixture is appropriately neutralized, and when there are insoluble materials in the reaction mixture the materials are removed by filtration of the reaction mixture; water is added to the reaction mixture and the mixture is extracted with an organic solvent immiscible with water such as ethyl acetate; the extract is washed with water, dried over anhydrous magnesium sulfate or the like and the solvent is removed by distillation to give the desired product. The product thus obtained, if necessary, can be further purified by a conventional procedure, for example, recrystallization, reprecipitation, or silica gel column chromatography.

According to the process of the present invention a γ-ketoacetal compound can be obtained through a simple procedure and in high yield as a high-purity product without using nitromethane.

The present invention is exemplified by some examples shown below. However, the present invention is not restricted by these examples.

EXAMPLE

Example 1

3-(5,5-Dimethyl-1,3-dioxan-2-yl)-1-(4-ethoxyphenyl)butan-1-one

2-Bromo-1-(4-ethoxyphenyl)ethan-2-one (5.0 kg) and N,N-bis(2-methylpropyl)-1-propenylamine (5.1 kg) were added to 20 liters of acetonitrile under an atmosphere of nitrogen and the mixture was stirred at around 50° C. for 1.5 hours. To the reaction mixture were added successively 20 liters of water, 5.0 kg of concentrated sulfuric acid, 3.2 kg of neopentyl glycol, and 0.5 kg of para-toluenesulfonic acid and the mixture was stirred at around 50° C. for 1.5 hours. After cooling the reaction mixture to the room temperature, crystals precipitated. These crystals were isolated by filtration to give 4.3 kg (yield 71%) of the title compound as white crystals.

$^1$H-NMR spectrum (400 MHz, CDCl$_3$) δ ppm: 0.71 (s, 3H), 1.03 (d, J=6.8 Hz, 3H), 1.18 (s, 3H), 1.44 (t, J=7.0 Hz, 3H), 2.42–2.52 (m, 1H), 2.78 (dd, J=16.6 Hz, J=8.5 Hz, 1H), 3.25 (dd, J=16.6 Hz, J=4.6 Hz, 1H), 3.41 (dd, J=11.0 Hz, J=3.7 Hz, 2H), 3.57–3.63 (m, 2H), 4.10 (q, J=7.0 Hz, 2H), 4.38 (d, J=3.7 Hz, 1H), 6.91 (d, J=8.7 Hz, 2H), 7.96 (d, J=8.7 Hz, 2H).

Example 2

3-(5,5-Dimethyl-1,3-dioxan-2-yl)-1-(4-ethoxyphenyl)butan-1-one

2-Bromo-1-(4-ethoxyphenyl)ethan-1-one (4.0 g) and N,N-bis(2-methylpropyl)-1-propenylamine (4.0 g) were added to 16 ml of dimethylacetamide under an atmosphere of nitrogen and the mixture was stirred between 50° C. and 55° C. for 2 hours. To the reaction mixture were added successively 1.6 g of paratoluenesulfonic acid and 2.1 g of neopentyl glycol and the mixture was stirred between 50° C. and 60° C. for 3 hours. After addition of 8 ml of water to the reaction mixture and cooling the reaction mixture to the room temperature, crystals precipitated. These crystals were isolated by filtration to give 3.7 g (yield 74%) of the title compound as white crystals. The $^1$H-NMR spectrum of the product is substantially identical with that of the product of Example 1.

Example 3

3-(5,5-Dimethyl-1,3-dioxan-2-yl)-1-(4-ethoxyphenyl)butan-1-one

2-Bromo-1-(4-ethoxyphenyl)ethan-1-one (4.0 g) and N,N-bis(2-methylpropyl)-1-propenylamine (4.0 g) were added to 16 ml of dimethylformamide under an atmosphere of nitrogen and the mixture was stirred between 50° C. and 55° C. for 2 hours. To the reaction mixture were added successively 1.6 g of paratoluenesulfonic acid and 2.1 g of neopentyl glycol and the mixture was stirred between 50° C. and 60° C. for 3 hours. After addition of 8 ml of water to the reaction mixture and cooling the reaction mixture to the room temperature, crystals precipitated. These crystals were isolated by filtration to give 3.7 g (yield 72%) of the title compound as white crystals. The $^1$H-NMR spectrum of the product is substantially identical with that of the product of Example 1.

Example 4

3-(5,5-Dimethyl-1,3-dioxan-2-yl)-1-(3,4-dimethylphenyl)butan-1-one

2-Bromo-1-(3,4-dimethylphenyl)ethan-1-one (220 g) and N,N-bis(2-methylpropyl)-1-propenylamine (249 g) were added to 990 ml of dimethylformamide under an atmosphere of nitrogen and the mixture was stirred at around 50° C. for 2 hours. After cooling the reaction mixture to 10° C., 990 ml of water, 170 g of neopentyl glycol and 173 g of concentrated sulfuric acid were added successively to the reaction mixture and the mixture was stirred at around 60° C. for 2 hours. After cooling the reaction mixture to the room temperature, crystals precipitated. These crystals were isolated by filtration to give 262 g (yield 83%) of the title compound as white crystals.

$^1$H-NMR spectrum (400 MHz, CDCl$_3$) δ ppm: 0.71 (s, 3H), 1.03 (d, J=6.8 Hz, 3H), 1.18 (s, 3H), 2.31 (s, 6H), 2.43–2.53 (m, 1H), 2.81 (dd, J=16.8 Hz, J=8.5 Hz, 1H), 3.26 (dd, J=16.7 Hz, J=4.8 Hz, 1H), 3.41 (dd, J=11.1 Hz, J=4.3 Hz, 2H), 3.58–3.63 (m, 2H), 4.39 (d, J=3.4 Hz, 1H), 7.20 (d, J=7.6 Hz, 1H), 7.72 (d, J=7.6 Hz, 1H), 7.76 (s, 1H).

Example 5

3-(5,5-Dimethyl-1,3-dioxan-2-yl)-1-(3,4-dimethylphenyl)butan-1-one

2-Bromo-1-(3,4-dimethylphenyl)ethan-1-one (6.2 g) and N,N-bis(2-methylpropyl)-1-propenylamine (6.8 g) were added to 25 ml of acetonitrile under an atmosphere of nitrogen and the mixture was stirred at around 50° C. for 4 hours. After cooling the reaction mixture to 10° C., 25 ml of water, 4.3 g of neopentyl glycol, 6.2 g of concentrated sulfuric acid and 0.62 g of para-toluenesulfonic acid were added to the reaction mixture and the mixture was stirred at around 60° C. for 1 hour. After cooling the reaction mixture to the room temperature, crystals precipitated. These crystals were isolated by filtration to give 6.6 g (yield 84%) of the title compound as white crystals.

The $^1$H-NMR spectrum of the product is substantially identical with that of the product of Example 4.

According to the process of the present invention a γ-ketoacetal compound can be obtained through a simple procedure and in high yield as a high-purity product without using nitromethane.

What is claimed is:

1. A process for the production of a compound of a formula (1) which process comprises (a) reacting a compound of a formula (2)

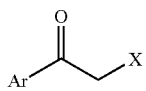

(2)

wherein Ar represents an unsubstituted $C_6$–$C_{10}$ aryl group or a $C_6$–$C_{10}$ aryl group substituted with at least one substituent independently selected from Substituent group α; Substituent group α is selected from the group consisting of a halogen atom, an unsubstituted $C_1$–$C_6$ alkyl group, a halogenated $C_1$–$C_6$ alkyl group, a hydroxyl group, a $C_1$–$C_6$ alkoxy group, a $C_1$–$C_6$ alkylthio group, a mercapto group, a $C_1$–$C_6$ alkylsulfonyl group and a sulfamoyl group; and X represents a halogen atom, with a compound of a formula (3)

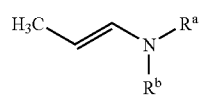

(3)

wherein $R^a$ and $R^b$ are the same or different and each represents independently an unsubstituted $C_1$–$C_6$ alkyl group; a $C_1$–$C_6$ alkyl group substituted with at least one $C_1$–$C_6$ alkoxy group; or a $C_3$–$C_6$ cycloalkyl group; or $R^a$ and $R^b$ taken together represent a $C_4$–$C_8$ alkylene group, in an inert solvent and hydrolyzing the resultant reaction product with an acid to afford a compound of a formula (4)

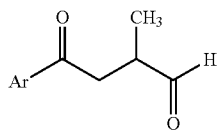

(4)

wherein Ar has the same meaning as that indicated above; and (b) reacting the compound of the formula (4) with a compound of a formula (5)

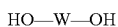 (5)

wherein W represents a $C_1$–$C_6$ alkylene group, in the presence of an acid to afford the compound of the formula (1)

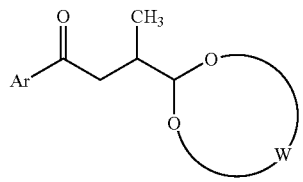

(1)

wherein Ar and W have the same meanings as those indicated above.

2. The process according to claim 1, wherein Ar is an unsubstituted phenyl group or a phenyl group substituted with at least one substituent independently selected from Substituent group α.

3. The process according to claim 1, wherein Ar is an unsubstituted phenyl group or a phenyl group substituted with at least one substituent independently selected from the group consisting of a methyl group, a methoxy group, an ethoxy group and a methylthio group.

4. The process according to claim 1, wherein Ar is a 4-methylphenyl group, a 3-methylphenyl group, a 4-methoxyphenyl group, a 4-ethoxyphenyl group, a 4-methylthiophenyl group, a 3,4-dimethylphenyl group or 3,4-dimethoxyphenyl group.

5. The process according to any one of claims 1 to 4, wherein X is a bromine atom or an iodine atom.

6. The process according to any one of claims 1 to 4, wherein X is a bromine atom.

7. The process according to claim 1, wherein $R^a$ and $R^b$ are the same or different and each represents independently an unsubstituted $C_2$–$C_5$ alkyl group; a $C_2$–$C_5$ alkyl group substituted with at least one $C_1$–$C_4$ alkoxy group; or a $C_4$–$C_6$ cycloalkyl group.

8. The process according to claim 1, wherein $R^a$ and $R^b$ are the same or different and each represents independently an isopropyl group, an isobutyl group, an isopentyl group, a 2-methoxyethyl group, a 3-methoxypropyl group, a 2-ethoxyethyl group, a cyclopentyl group, or a cyclohexyl group.

9. The process according to claim 1, wherein $R^a$ and $R^b$ are both an isobutyl group.

10. The process according to claim 1, wherein W is a straight or branched chain $C_3$–$C_5$ alkylene group.

11. The process according to claim 1, wherein W is a straight chain $C_3$–$C_5$ alkylene group.

12. The process according to claim 1, wherein W is a 2-methyltrimethylene group or 2,2-dimethyltrimethylene group.

13. The process according to claim 1, wherein Ar is 4-ethoxyphenyl.

14. A process for the production of a compound of a formula (7)

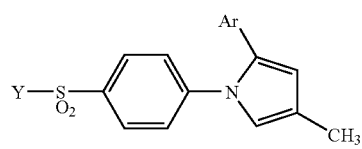

(7)

wherein Ar represents an unsubstituted $C_6$–$C_{10}$ aryl group or a $C_6$–$C_{10}$ aryl group substituted with at least one substituent independently selected from Substituent group α; Substituent group α is selected from the group consisting of a halogen atom, a $C_1$–$C_6$ alkyl group, a halogenated $C_1$–$C_6$ alkyl group, a hydroxyl group, a $C_1$–$C_6$ alkoxy group, a $C_1$–$C_6$ alkylthio group, a mercapto group, a $C_1$–$C_6$ alkylsulfonyl group and a sulfamoyl group; and Y represents a methyl group or an amino group, which comprises:
(a) reacting a compound of a formula (2)

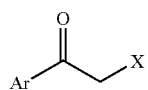

(2)

wherein Ar represents an unsubstituted $C_6$–$C_{10}$ aryl group or a $C_6$–$C_{10}$ aryl group substituted with at least one substituent independently selected from Substituent group α; Substituent group α is selected from the group consisting of a halogen atom, a $C_1$–$C_6$ alkyl group, a halogenated $C_1$–$C_6$ alkyl group, a hydroxyl group, a $C_1$–$C_6$ alkoxy group, a $C_1$–$C_6$ alkylthio group, a mercapto group, a $C_1$–$C_6$ alkylsulfonyl group and a sulfamoyl group; and X represents a halogen atom, with a compound of a formula (3)

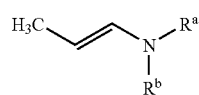

(3)

wherein $R^a$ and $R^b$ are the same or different and each represents independently an unsubstituted $C_1$–$C_6$ alkyl group; a $C_1$–$C_6$ alkyl group substituted with at least one $C_1$–$C_6$ alkoxy group; or a $C_3$–$C_6$ cycloalkyl group; or $R^a$ and $R^b$ taken together represent a $C_4$–$C_8$ alkylene group, in an inert solvent; hydrolyzing the resultant product with an acid to afford a compound of a formula (4)

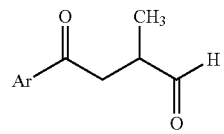

(4)

wherein Ar has the same meaning as that indicated above; and
(b) reacting the compound of the formula (4) with a compound of a formula (5)

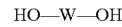

HO—W—OH (5)

wherein W represents a $C_1$–$C_6$ alkylene group, in the presence of an acid to afford a compound of a formula (1)

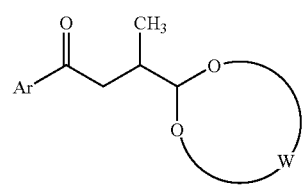

(1)

wherein Ar and W have the same meanings as those indicated above; and
(c) reacting the compound of the formula (1) with a compound of a formula (6)

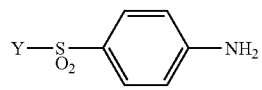

(6)

wherein Y is a methyl group or an amino group to afford the compound of the formula (7).

15. The process according to claim 14, wherein Y is an amino group.

* * * * *

UNITED STATES PATENT AND TRADEMARK OFFICE
CERTIFICATE OF CORRECTION

| | | |
|---|---|---|
| PATENT NO. | : 7,176,323 B2 | Page 1 of 1 |
| APPLICATION NO. | : 11/055645 | |
| DATED | : February 13, 2007 | |
| INVENTOR(S) | : Okazaki et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 174 days Delete the phrase "by 174 days" and insert -- by 178 days--

Signed and Sealed this

Twenty-fourth Day of July, 2007

JON W. DUDAS
*Director of the United States Patent and Trademark Office*